US006620437B2

(12) United States Patent
Ewbank et al.

(10) Patent No.: US 6,620,437 B2
(45) Date of Patent: Sep. 16, 2003

(54) WATER-IN-OIL MICROEMULSION FOR PROVIDING COSMETIC ATTRIBUTES TO FABRIC SOFTENING BASE COMPOSITION

(75) Inventors: Eric Ewbank, Kraainem (BE); Dominique Tummers, Seraing (BE)

(73) Assignee: Colgate-Palmolive Co., New York, NY (US)

( * ) Notice: Subject to any disclaimer, the term of this patent is extended or adjusted under 35 U.S.C. 154(b) by 95 days.

(21) Appl. No.: 09/783,829

(22) Filed: Feb. 15, 2001

(65) Prior Publication Data

US 2002/0010104 A1 Jan. 24, 2002

Related U.S. Application Data

(63) Continuation-in-part of application No. 09/126,308, filed on Jul. 30, 1998, now abandoned.

(51) Int. Cl.[7] .......................... A61K 9/14; A01N 25/00

(52) U.S. Cl. ...................... 424/489; 510/101; 510/312; 510/524; 510/525; 510/526; 514/937

(58) Field of Search .......................... 424/489; 510/101, 510/312, 524–526; 514/937

(56) References Cited

U.S. PATENT DOCUMENTS

| | | | | | |
|---|---|---|---|---|---|
| 5,447,644 | A | * | 9/1995 | Guenin et al. | 258/8.6 |
| 5,525,245 | A | * | 6/1996 | Grandmaire et al. | 252/8.8 |
| 5,656,585 | A | * | 8/1997 | Grandmaire et al. | 510/524 |

FOREIGN PATENT DOCUMENTS

| | | | |
|---|---|---|---|
| EP | 0813862 | | 12/1997 |
| WO | 0006690 | | 2/2000 |
| WO | 00/06690 | * | 2/2000 |
| WO | 0066703 | | 11/2000 |

* cited by examiner

*Primary Examiner*—Bennett Celsa
(74) *Attorney, Agent, or Firm*—Bernard Lieberman

(57) ABSTRACT

A perfume-containing water-in-oil microemulsion is provided which is capable of being mixed with an aqueous fabric softener base composition to provide perfume thereto. The use of the defined microemulsion enables the addition of perfume as well as other cosmetic attributes to an aqueous base composition under conditions of low shear while avoiding any problems of gelation or physical instability in the finished fabric softener product.

15 Claims, No Drawings

WATER-IN-OIL MICROEMULSION FOR PROVIDING COSMETIC ATTRIBUTES TO FABRIC SOFTENING BASE COMPOSITION

This application is a continuation-in-part of U.S. application Ser. No. 09/126,308 filed Jul. 30, 1998 now abandoned, the disclosure of which is incorporated herein by reference.

FIELD OF INVENTION

This invention relates to a composition and method for "post-adding" cosmetic attributes to a fabric softening base composition at the final stage of its manufacture. More particularly it relates to a water-in-oil microemulsion which is suitable for containing adjuvants such as perfume or colorant and which can be readily mixed with a fabric softening base composition with only a minimum amount of shear and without adversely affecting its physical stability.

BACKGROUND OF THE INVENTION

Perfumes and colorants are routinely introduced into liquid fabric softening compositions to provide appealing cosmetic attributes for the consumer. The introduction of perfume, for example, to a liquid softening composition, is meant to leave a pleasant and lasting fragrance on the treated fabrics. The colorant is intended to provide a visually pleasing product as well as convey to the consumer an overall impression of softness and quality. From a marketing standpoint, perfumes and colorants are attributes which allow the formulator a degree of flexibility to provide product variety for a given softening technology or for a fixed fabric softening base composition.

Although perfume, on a weight basis, is invariably a very minor component of a commercial fabric softener composition, its introduction into the composition in an efficient manner is a subject of much concern in the formulation art. This is particularly true for concentrated fabric softeners containing more than about 10% by weight of active softening ingredients insofar as the aqueous softener base compositions tend to gel in the presence of water-immiscible perfume. This tendency of gel formation is particularly problematic when the water-immiscible perfume is poorly dispersed in the aqueous emulsion which constitutes the softening base composition.

Undesirable thickening or gelation of a softener base composition has significant drawbacks: it reduces the effective shelf life of the final product and adversely affects consumer acceptance for a softener product which upon use has thickened to an unexpectedly viscous mass instead of meeting the consumers expectation of being essentially free-flowing. As a result the prior art has addressed itself to overcoming the pervasive problems of gelation and the formation of high viscosity liquids which accompany the introduction of water-insoluble perfumes into aqueous fabric softener base compositions.

U.S. Pat. No. 5,447,644 to International Flavors & Fragrances (IFF) describes a method to avoid gelation of the softening composition resulting from the introduction of increased levels of perfume into a softener base composition. According to this method there is first formed an aqueous microemulsion by mixing the perfume with a defined nonionic surfactant under conditions of high shear to uniformly disperse the perfume in the surfactant/water mixture. The perfume-containing microemulsion is then mixed with a fabric softener base formulation to form the final fabric softener composition. A high shear mixer is required for this mixing operation.

Accordingly, there remains a need in the art for a method to readily introduce fragrances and colorants into a fabric softener base at the very end of the manufacturing process or even by the consumer himself in the home under very gentle mixing conditions, avoiding the need for high shear mechanical agitation and equipment. Further, there is a need for a method which apart from incorporating perfume or colorants into a base formulation, will do so without adversely impacting the rheological and physical stability of the final product.

SUMMARY OF THE INVENTION

In accordance with the present invention there is provided a perfume-containing water-in-oil microemulsion capable of being mixed with a perfume-free fabric softener base composition which is in the form of an aqueous emulsion so as to disperse perfume in said aqueous emulsion under conditions of low shear while avoiding any problem of gelation to thereby provide a physically stable perfume-containing liquid fabric softening composition, said water-in-oil microemulsion comprising:

(a) from about 5% to about 80%, by weight, of a surfactant fabric softener selected from the group consisting of:

(i) diester quaternary ammonium compounds having the structural formulae as follows:

(1)

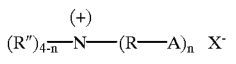

wherein each

A is independently C(O)O—R' or —O(O)C—R';

R is a lower alkyl group having 1 to about 4 carbon atoms;

R' is an alkyl or alkenyl group having 8 to about 22 carbon atoms;

R" is independently a lower alkyl radical having 1 to about 6 carbon atoms or hydroxyl alkyl group or H;

n is an integer having a value of 1 to about 3; and $X^-$ is a softener compatible anion; and (2)

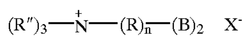

wherein B is independently A or $(R)_n$-A; and A, R, R" and n are as defined above; and (3)

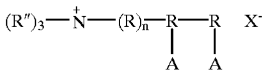

wherein A, R, R" and n are as defined above; and/or (ii) diamido ammonium compounds having the formula:

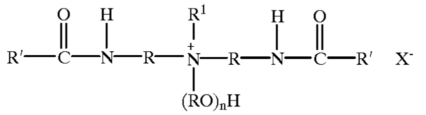

wherein n, $X^-$ and R' are as defined above, $R^1$ is a lower alkyl radical having 1 to about 4 carbon atoms or hydrogen, and R is an alkylene radical having 2 to about 4 carbon atoms;

(b) from about 2% to about 50%, by weight, of an organic solvent;

(c) from about 15% to about 70%, by weight, of a water-immiscible perfume, components (a), (b) and (c) comprising the oily phase of said microemulsion;

(d) from 0% to about 1% of a colorant; and (e) from about 0.5% to about 26%, by weight, of water; said microemulsion being free of an anionic surfactant, and having a weight ratio of said oily phase to water of from about 3:1 to about 200:1 with the proviso that for weight ratios of said oily phase to water of below 9:1, the weight ratio of perfume to solvent is less than 1:1; and/or the surfactant fabric softener (a) is greater than 25%, by weight, and wherein the percentages of components (a), (b) and (c) are selected so that the resulting composition forms a water-in-oil microemulsion.

Danielsson and Lindman, "The definition of Microemulsion", Colloids and Surfaces, 3 (1981), 391–392, Elsevier Scientific Publishing Company, have defined a "microemulsion" as 'a system of water, oil and amphiphile which is a single optically isotropic and thermodynamically stable liquid solution'. This definition of microemulsion is used herein in describing the present invention.

In accordance with the above definition, a microemulsion has the following characteristics/properties:

i) Clear ii) It is free of lyotropic liquid crystalline system (i.e. it is isotropic)

iii) It has relatively low viscosity iv) It is formed spontaneously by simple mixture/agitation of all components (i.e. it is thermodynamically stable)

More detailed information concerning various aspects of microemulsion systems such as definition, phase behavior, structure, low interfacial tensions and dynamics, is disclosed in R. Zana's article, 'Microemulsions' in Heterogeneous Chemistry Reviews, Vol. 1, 145–157 (1994), edited by John Wiley & Sons Ltd, the disclosure of which is incorporated herein by reference.

The present invention also provides a method for introducing a perfume into a perfume-free fabric softener base composition which is in the form of an aqueous emulsion under conditions of low shear and without adversely affecting its physical stability comprising the steps of:

(a) providing a perfume-containing water-in-oil microemulsion as defined above; and (b) mixing an amount of said water-in-oil microemulsion sufficient to contain the desired amount of perfume with said fabric softener base composition under conditions of low shear thereby causing the inversion of said microemulsion and the dispersion of the perfume to form a physically stable perfume-containing liquid fabric softening composition.

The water-in-oil microemulsion compositions of the invention are predominantly comprised of the oily phase as defined above, namely, the cationic surfactant fabric softener, the organic solvent and the water-insoluble perfume. To form a composition in the desired phase of a water in oil microemulsion, the amount of water should generally be no greater than about 30%, by weight, and preferably, from about 5% to about 25%, by weight.

The preferred diester quaternary ammonium surfactants for use herein are the dioleyl diester "quats" represented by equation (1). Particularly preferred is methyl bis-[ethyl (oleyl)]-2-hydroxyethyl ammonium methyl sulfate, commonly referred to as "DODEQ".

The present invention is predicated on the discovery that cosmetic attributes such as perfume and colorant can be readily "post-added" to an aqueous fabric softening base composition at the final stage of its manufacture by using a water-in-oil microemulsion as herein defined as the vehicle to be added to and mixed with the aqueous emulsion to form the finished product. The water-in-oil microemulsion is incorporated into the softening base composition under conditions of gentle agitation or low shear, using a sufficient amount to provide the desired level of perfume to the finished product. The microemulsion undergoes an inversion upon dilution in the aqueous emulsion which serves to efficiently disperse the perfume or colorant throughout the composition without concomitant problems of gelation or product instability.

Accordingly, the present invention provides important advantages from the standpoint of manufacturing a softening product composition as well as in insuring the integrity of the final product itself. The essence of the present invention is an oil in water microemulsion which can be readily formed at room temperature with no need for high shear forces or elaborate mixing equipment. And with regard to the finished product, it is clear that the introduction of cosmetic attributes into a softening base composition is accomplished without adversely compromising the rheology or physical stability of the resulting product.

DETAILED DESCRIPTION OF THE INVENTION

Diester quaternary ammonium surfactant fabric softeners, represented by equation (1) are preferred for use herein and are commercially available from Stepan Co. as Stepantex and from KAO Corp. as Tetranyl but can also be synthesized by the reaction of two moles of a fatty acid with a trialkanolamine, preferably, triethanolamine followed by methylation with dimethyl sulfate or an alkyl halide such as, methyl iodide. In a preferred mode the fatty acid is oleic acid. For economical reasons it has been found that Soya fatty acids are a practical source for this purpose consisting of about 3% myristic acid, about 5% palmitic acid, about 5% palmitoleic acid, 1.5% stearic acid, 72.5% oleic acid and about 13% linoleic acid. Other sources of useful fatty acids are those obtained from the saponification of beef tallow, butter, corn oil, cottonseed oil, lard, olive oil, palm oil, peanut oil, cod liver oil, coconut oil and the like.

A preferred diester quaternary ammonium surfactant fabric softener is methyl bis[ethyl(oleyl)]-2-hydroxyethyl ammonium methyl sulfate. Other diesters useful in the practice of this invention include:

methyl bis-[ethyl(coconut)]-2-hydroxyethyl ammonium methyl sulfate
methyl bis-[ethyl(decyl)]-2-hydroxyethyl ammonium methyl sulfate
methyl bis-[ethyl(dodecyl)]-2-hydroxyethyl ammonium methyl sulfate
methyl bis-[ethyl(lauryl)]-2-hydroxyethyl ammonium methyl sulfate
methyl bis-[ethyl(palmityl)]-2-hydroxyethyl ammonium methyl sulfate
methyl bis-[ethyl(soft-tallow)]-2-hydroxyethyl ammonium methyl sulfate, and the like.

The designation of the terms coconut and soft-tallow indicate mixtures of esters corresponding to the fatty acid source.

In the preparation of the diester quaternary ammonium surfactants, a certain amount of the triester homolog may be produced as an impurity.

The term "perfume" is used herein in its ordinary sense to refer to and include any non water-soluble fragrant substance or mixture of substances including natural (i.e., obtained by extraction of flower, herb, blossom or plant), artificial (i.e., a mixture of natural oils or oil constituents) and synthetic (i.e., a single or mixture of synthetically produced substance) odoriferous substances. Typically perfumes are complex mixtures of blends of various organic compounds, such as, esters, ketones, hydrocarbons, lactones, alcohols, aldehydes, ethers, aromatic compounds and varying amounts of essential oils (e.g., terpenes) such as from about 0% to about 80%, usually from about 10% to 70% by weight, the essential oils themselves being volatile odoriferous compounds and also serving to dissolve the other components of the perfume. The precise composition of the perfume has no particular effect on fabric softening so long as it meets the criteria of water immiscibility and pleasant odor.

Organic solvents suitable for use in this invention include: aliphatic alcohols having 1 to about 6 carbon atoms, such as, ethanol, propanol, isopropanol, n-butanol, isobutanol, t-butanol, n-pentanol, isopentanol, sec-pentanol, n-hexanol, isohexanol, other isomers and the like; aliphatic polyalcohols, such as, ethylene glycol, propylene glycol, butylene glycol, diethylene glycol, dipropylene glycol, 1,4-butanediol, 2-methyl-pentanediol, hexane triol, tripropylene glycol, pentaerythritol, glycerol, sorbitol, and the like; aliphatic ethers, such as, ethylene glycol monobutyl ether (EGMBE), diethylene glycol monobutyl ether(DEGMBE), diethylene glycol dimethyl ether, triethylene dimethyl ether, ethylene glycol monomethyl ether, propylene glycol monoethyl ether, dipropylene glycol monomethyl ether, dipropylene glycolpropyl ether(DPnP), dipropylene glycolbutyl ether(DPnB), tripropylene glycol monomethyl ether, methoxy methyl butanol, and the like; aliphatic esters, such as, methyl lactate, ethyl lactate, isopropyl lactate, butyl lactate, dibasic esters of carboxylic acids, ethoxy ethyl acetate, propylene glycol butyl ether acetate, and butoxy ethyl acetate.

Among the preferred organic solvents for use herein are dipropylene glycol methyl ether (DPM); dipropylene glycol monobutyl ether (DPnB); and ethylene glycol monobutyl ether (EGMBE).

In the water in oil microemulsion compositions in accordance with the invention, the weight range of cationic surfactant is generally from about 5% to about 80%, and preferably from about 10% to about 60%, by weight; the weight range of the organic solvent is generally from about 2% to about 50%, and preferably from about 4% to about 40%, by weight; and the weight range of the water-immiscible perfume is generally from about 5% to about 80%, and preferably from about 15% to about 70%, by weight. The water content is generally from about 0.5% to about 30%, and preferably from about 5% to about 26%, by weight. The weight ratio of the defined oily phase to water is generally from about 3:1 to about 200:1, preferably from about 5:1 to 50:1, and most preferably from about 5:1 to about 20:1 with the proviso that if the weight ratio of said oily phase water is below 9:1, then either or both of the following must occur in order to form a water-in-oil microemulsion composition: (i) the weight ratio of perfume to solvent must be less than 1:1; or (ii) the surfactant fabric softener must be greater than 25% by weight.

The microemulsions of the invention have a particle size between 10 and 100 nanometers. At particle sizes below about 50 nanometers, the microemulsions are generally clear. The microemulsions are formed by simply combining the above-described components of the composition under gentle agitation or low shear. Conventional mixing equipment known to those skilled in the art is sufficient for this purpose. All of the components described herein, both required and optional, must be normally liquid, namely, liquid at ambient room temperatures. Accordingly, there is no need for heating during the preparation of the microemulsions.

The invention is further described in the examples which follow. All parts and percentages are by weight unless otherwise specified.

Microemulsion compositions/area in a pseudo-ternary phase diagram (i.e. 4 components) were basically determined on a clear/turbid criteria basis by mixing three of the components and titrating with incremental amounts of the fourth component. Generally, 3.0 g of a mixture consisting of organic solvent (or mixture of), water-immiscible perfume and water, were introduced in a suitable/fixed ratio, and then titrated with DODEQ (dioleyl diesterquat). Samples were mixed at RT using a magnetic stirrer operating at 100–150 rpm after which they were allowed to stand for few minutes before visual examination for clarity/tubidity. Clear samples were further examined under a polarizing microscope to check that the liquids were isotropic. By this method, estimated regions for microemulsion compositions were located on pseudo-ternary phase diagrams. Some compositions located inside these microemulsion areas were selected to illustrate the present invention.

DESCRIPTION OF CHEMICALS AND METHODS OF PREPARATION USED IN THE EXAMPLES BELOW

Chemicals

The water-in-oil microemulsions contain dioleyl diester quat (DODEQ) as described hereinabove. The formula of DODEQ is as follows:

(I)

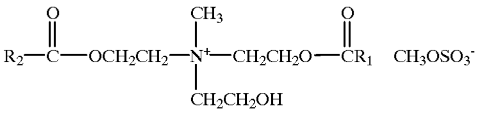

wherein $R_1$ and $R_2$ are $C_{17}H_{34}$, unsaturated alkyl chains from oleic acid.

DODEQ is commercially available from KAO as Tetranyl or from Stepan Co. as Stepantex. It is synthesized by the reaction of two moles of oleic acid with triethanolamine followed by methylation with dimethyl sulfate.

For purposes of economy, oleic acid may be replaced by olive fatty acids in the synthesis of DODEQ, such olive fatty acids comprising 14% palmitic acid, 2% palmitoleic acid, 2% stearic acid, 64% oleic acid, 16% linoleic acid and 2% linolenic acid. Such material is available from KAO under the name Tetranyl AO-2.

The water-soluble dyes used in the examples are marketed under the names Liquitint Royal Blue, Liquitint Yellow LP and Liquitint Nature Green, by Milliken Chemical company.

The fabric softening base compositions contain two principal softening compounds:

(i) a dialkyl-amidoamine compound commercially available as Rewopal V3340 from Rewo; and (ii) a dialkyl esterquat sold as Tetranyl AT175 by KAO.

The dialkyl amidoamine compounds have the general structural formula as follows:

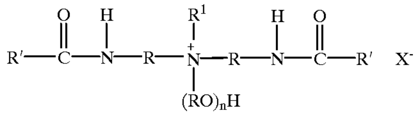

wherein n is an integer of from 1 to 3; R is an alkylene radical having 2 to 4 carbon atoms; R' is an alkyl or alkenyl group having 8 to about 22 carbon atoms; $R^1$ is a lower alkyl group having 1 to about 4 carbon atoms or hydrogen; and $X^-$ is a softener compatible anion.

Method of Preparing Softening Base Composition

The softening ingredients are each melted, mixed together with stirring and maintained at about 60 to 70° C. The mixture of molten softening active compounds is added to heated (60–70° C.) deionized water with stirring using a 4-pitched blade impeller. The hot water mixture is stirred for 10 to 15 min at about 400 rpm in order to emulsify the molten actives. For concentrated compositions, the stirring speed is increased to 700–800 rpm as the viscosity of the emulsion increases. When required in the formula composition, hydrochloric acid is first introduced separately in the water prior to the addition of the molten softening ingredients.

The emulsion is allowed to cool down to 30° C. while stirring it at 300–400 rpm. When appropriate, the particle size distribution of the emulsion is further reduced, subjecting the product to high pressure homogenization. This step reduces the viscosity of the composition. Calcium chloride, preservative, sequestering agent and other optional ingredients such as the thickener, are all introduced sequentially with stirring into the cooled product.

EXAMPLE 1

Preparation of Perfume-Containing Microemulsion

Compositions 1 through 6 were prepared following the procedures described above, each composition having varying weight percentages of the four principal components: cationic surfactant; organic solvent; perfume; and water. The ratio of perfume to organic solvent was kept constant at 60:40. The compositions are shown in Table 1 along with observations concerning the appearance of the resulting composition and whether it is within the invention, namely, it formed a water in oil microemulsion, or outside the invention, by forming an emulsion.

TABLE 1

| COMPONENT | 1 | 2 | 3 | 4 | 5 | 6 |
|---|---|---|---|---|---|---|
| DODEQ | 15% | 50% | 50% | 25% | 15% | 25% |
| Organic solvent (DPM) (1) | 32 | 18 | 14 | 26 | 23.6 | 24 |
| Perfume | 48 | 27 | 21 | 39 | 35.4 | 36 |
| Water | 5 | 5 | 15 | 10 | 26 | 15 |
| Appearance of composition | Clear | Clear | Clear | Clear | Turbid | Turbid |
| Microemulsion (M)/Emulsion (E) | M | M | M | M | E | E |

(1) DPM refers to dipropylene glycol methyl ether

As noted in Table 1, Compositions 1–4 are w/o microemulsions within the invention; compositions 5 and 6 are emulsions.

EXAMPLE 2

Preparation of W/O Microemulsion Containing Perfume and Colorant

Compositions 7 through 9 were prepared containing a fixed level of perfume and a varying amount of colorant. The compositions are shown below in Table 2 along with observations concerning the physical appearance of the resulting composition.

TABLE 2

| COMPONENT | 7 | 8 | 9 |
|---|---|---|---|
| DODEQ | 25% | 25% | 15% |
| Organic solvent (DPM) | 26 | 26 | 32 |
| Perfume | 39 | 39 | 48 |
| Water | 9.95 | 9.5 | 4.9 |
| Colorant | 0.05 | 0.5 | 0.1 |
| Appearance of composition | clear(1) | clear(1) | clear(1) |
| Microemulsion (M)/Emulsion (E) | M | M | M |

(1) Clear but colored

EXAMPLE 3

The Effect of Increasing the Level of Solvent on the Microemulsion Region of the Phase Diagram To demonstrate the effect of increased levels of organic solvent on the region of microemulsion compositions, compositions 5, 6, 10, 11 and 12 were prepared wherein the weight ratio of fragrance to organic solvent was varied. The compositions are shown in Table 3 along with observations concerning the appearance of the resulting composition.

TABLE 3

| COMPONENT | 5 | 10 | 11 | 6 | 12 |
|---|---|---|---|---|---|
| DODEQ | 15% | 15% | 15% | 25% | 25% |
| Perfume + organic solvent (DPM) | 59% | 59% | 59% | 60% | 60% |
| Ratio of Perfume to organic solvent | 60:40 | 60:50 | 32:68 | 60:40 | 50:50 |
| Water | 26% | 26% | 26% | 15% | 15% |
| Appearance of composition | Turbid | Turbid | Clear | Turbid | Clear |
| Microemulsion (M)/Emulsion (E) | E | E | M | F | M |

Compositions 5 and 6 are two compositions from Example 1, which are outside of the invention but are included in Table 3 as comparative compositions. Table 3 demonstrates that by changing the ratio of Perfume to organic solvent, it is possible to convert a turbid emulsion into a clear fragrance microemulsion suitable for the present invention. Thus, a comparison of composition 11, a clear w/o microemulsion, with the emulsion compositions 5 and 10 which are outside the invention underscores the criticality of the perfume to organic solvent ratio. Similarly a comparison of compositions 6 and 12 demonstrates that by properly adjusting the ratio of perfume to organic solvent, a composition which is outside the invention (composition 6), can be reformulated to provide a clear w/o microemulsion (composition 12).

EXAMPLE 4

Preparation of W/O Microemulsions with Different Classes of Solvents

Compositions 13 through 18 were prepared to demonstrate the ability to prepare microemulsions in accordance with the invention using organic solvents from the following classes: ethers, esters, glycols and alkanols. The compositions are shown in Table 4 below along with observations concerning the appearance of the resulting composition.

TABLE 4

| COMPONENT | 13 | 14 | 15 | 16 | 17 | 18 |
|---|---|---|---|---|---|---|
| Water | 10% | 10% | 10% | 10% | 10% | 10% |
| DODEQ | 25 | 25 | 25 | 25 | 25 | 25 |
| Perfume | 32.5 | 32.5 | 32.5 | 32.5 | 32.5 | 32.5 |
| ORGANIC SOLVENT | | | | | | |
| DPM (Ether) | 32.5 | — | — | — | — | 16.25 |
| DPnB (Ether) | — | — | — | — | — | 16.25 |
| EGMBE (Ether) | — | 32.5 | — | — | — | — |
| Hexylene glycol (Glycol) | — | — | 32.5 | — | — | — |
| Butanol (Alkanol) | — | — | — | 32.5 | — | — |
| Methyl lactate (Ester) | — | — | — | — | 32.5 | — |
| Appearance of Composition | Clear | Clear | Clear | Clear | Clear | Clear |
| Microemulsion (M)/Emulsion (E) | M | M | M | M | M | M |

EXAMPLE 5

Dispersion of Perfume-Containing Microemulsion into a Softening Base

The dispersion properties of a perfume-containing microemulsion in accordance with the invention were demonstrated using two different softening base compositions and comparing same with dispersion into 100% water. The perfume micromemulsion composition was comprised of the following: 39% perfume; 26% EGMBE organic solvent; 25% DODEQ; 0.48% Liquitint Royal Blue colorant (4% solution); and balance water.

A first softening base composition ("AA/EstQ" base) was comprised of the following: 2.74% amidoamine (Rewopal V3340); 1.64% Esterquat (Tetranyl AT1-75); 0.29% glyceryl monooleate; 0.3% hydrochloric acid (25% solution); 0.074% lactic acid (Purac SP80); and balance water.

The second softening base composition ("EstQ/FA" base) was comprised of the following: 3.9% Esterquat (Tetranyl AT1-75); 0.83% $C_{16-18}$ fatty alcohol; 0.2% alcohol ethoxylate ($C_{13-15}$ fatty alcohol 20EO); 0.1% amino trimethyl phosphonic acid; 0.063% lactic/lactate buffer solution; 0.20% polyacrylate thickener; and balance water.

The perfume microemulsion was introduced into each of the above-described softening base compositions at a level of 1.28%, by weight, under very low shear conditions. Mixing was achieved with an Oscell-12 shaker operating for 12 seconds at 700 oscillations per minute. Particle size of the softening base compositions was measured before and after the addition of the perfume microemulsion. For purposes of comparison, dispersion "as is" was measured by post-adding pure perfume to each softening base.

TABLE 5

PARTICLE SIZE OF SOFTENING BASE BEFORE AND AFTER POST-ADDITION OF PERFUME

| SOFTENING BASE | PARTICLE SIZE ($\mu$m) BEFORE ADDITION | PARTICLE SIZE ($\mu$m) AFTER POST-ADDITION WITH Perfume Microemulsion | Perfume "AS IS" |
|---|---|---|---|
| AA/EstQ | 2.5 | 2.8 | 72.0 |
| EstQ/FA | 4.2 | 5.0 | 22.0 |
| Water | — | 24.5 | >100 |

As demonstrated by the data, dispersion of the perfume into the softening base was efficiently carried out using the microemulsion of the invention. The addition of pure perfume ("as is") under the same mixing conditions resulted in an unacceptable dispersion of perfume into the softening base.

EXAMPLE 6

The purpose of this Example was to demonstrate the inoperability of a perfume-containing water-in-oil microemulsion which is not formulated in accordance with the invention.

The microemulsion composition was comprised of the following:

(a) 35.8%, by weight, sodium lauryl ether sulfate surfactant;

(b) 15.4% water;

(c) 24.4% perfume (d) 24.4% DPM organic solvent.

The softening base composition was comprised of the following:

(a) 9.2%, by weight, amidoamine (Rewopal V3340);

(b) 4.5% Esterquat (Tetranyl AT1-75);

(c) 1.0% glycerol monooleate;

(d) 1.4% HCI (25% solution);

(e) 0.15% calcium chloride (20% solution);

(f) 0.25% lactic/lactate buffer solution;

(g) 0.4% Liquitint Royal Blue (4% solution).

Five percent by weight of the perfume-containing w/o microemulsion composition was added to the softening base composition under gentle mixing conditions. A precipitate was observed to form indicating a phase separation and product instability.

What is claimed is:

1. A perfume-containing water-in-oil microemulsion capable of being mixed with a perfume-free fabric softener base composition which is in the form of an aqueous emulsion so as to disperse perfume in said aqueous emulsion under conditions of low shear while avoiding any problem of gelation to thereby provide a physically stable perfume-containing liquid fabric softening composition, said water-in-oil microemulsion comprising:

(a) from about 5% to about 80%, by weight, of a surfactant fabric softener selected from the group consisting of a dioleyl diester quaternary ammonium compound represented by the formula:

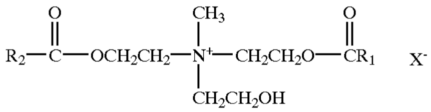

wherein $R_1$ and $R_2$ are $C_{17}H_{34}$, unsaturated alkyl chains from oleic acid, or olive fatty acids; and $X^-$ is a softener compatible anion;

(b) from about 2% to about 50%, by weight, of an organic solvent;

(c) from about 15% to about 70%, by weight, of a water-immiscible perfume, components (a), (b) and (c) comprising the oily phase of said microemulsion;

(d) from 0% to about 1% of a colorant; and (e) from about 0.5% to about 26%, by weight, of water; said microemulsion being free of an anionic surfactant, and having a weight ratio of said oily phase to water of from about 3:1 to about 200:1 with the proviso that for weight ratios of said oily phase to water of below 9:1, the weight ratio of perfume to organic solvent is less than 1:1; and/or the surfactant fabric softener (a) is greater than 25%, by weight, and wherein the percentages of components (a), (b) and (c) are selected so that the resulting composition forms a water-in-oil microemulsion.

2. A microemulsion as in claim 1 wherein the diester quaternary ammonium surfactant is methyl bis[ethyl (oleyl)]-2-hydroxyethyl ammonium methyl sulfate.

3. A microemulsion as in claim 1 wherein said organic solvent is an aliphatic alcohol having from 1 to about 6 carbon atoms.

4. A microemulsion as in claim 3 wherein said organic solvent is n-butanol.

5. A microemulsion as in claim 1 wherein said organic solvent is an aliphatic polyalcohol.

6. A microemulsion as in claim 5 wherein said polyalcohol is hexylene glycol.

7. A microemulsion as in claim 1 wherein said organic solvent is an aliphatic ether.

8. A microemulsion as in claim 7 wherein said ether is dipropylene glycol methyl ether.

9. A microemulsion as in claim 7 wherein said ether is dipropylene glycol n-butyl ether.

10. A microemulsion as in claim 7 wherein said ether is ethylene glycol monobutyl ether.

11. A microemulsion as in claim 1 wherein said organic solvent is an aliphatic ester.

12. A microemulsion as in claim 11 wherein said ester is methyl lactate.

13. A microemulsion as in claim 1 wherein said fabric softener base composition contains a diester quaternary ammonium softener.

14. A method for introducing a perfume into a perfume-free fabric softener base composition which is in the form of an aqueous emulsion under conditions of low shear and without adversely affecting its physical stability comprising the steps of:

(a) providing a perfume-containing water-in-oil microemulsion as defined in claim 1; and (b) mixing an amount of said water-in-oil microemulsion sufficient to contain the desired amount of perfume with said fabric softener base composition under conditions of low shear thereby causing the inversion of said microemulsion and the dispersion of the perfume in said aqueous emulsion to form a physically stable perfume-containing liquid fabric softening composition.

15. A method of imparting softness to fabrics concomitant with a perfume fragrance comprising contacting the fabrics with a softening effective amount of the liquid fabric softening composition formed in claim 14.

* * * * *